United States Patent [19]

Collineau et al.

[11] 3,982,183
[45] Sept. 21, 1976

[54] PARTICLE SIZING APPARATUS
[75] Inventors: Claude Jean Collineau, Margency;
Jacques Andre Pontigny,
Montmorency, both of France
[73] Assignee: Coulter Electronics, Inc., Hialeah, Fla.
[22] Filed: Feb. 20, 1975
[21] Appl. No.: 551,328

[52] U.S. Cl. .................. 324/71 CP; 235/92 PC; 354/115
[51] Int. Cl.² ..................................... G01N 27/00
[58] Field of Search .............. 324/71 CP, 115; 235/92 PC

[56] References Cited
UNITED STATES PATENTS

| | | | |
|---|---|---|---|
| 3,560,847 | 2/1971 | Boyd et al. | 324/71 |
| 3,757,213 | 9/1973 | Coulter et al. | 324/71 CP |
| 3,873,918 | 3/1975 | Talbert | 324/71 CP |
| 3,887,868 | 6/1975 | Guggenbühl | 324/71 CP |

Primary Examiner—R. V. Rolinec
Assistant Examiner—Vincent J. Sunderdick
Attorney, Agent, or Firm—Silverman & Cass, Ltd.

[57] ABSTRACT

Apparatus for obtaining automatically the distribution of volume or mass of particles suspended in a sample. The sample is analyzed in successive sequences or sections each representing a magnitude of given particles. A counter is provided for counting the particles in the sections, and a measuring circuit determines a value which is proportional to the time required by the counter to obtain the number of counted particles. The values are transmitted by a differential circuit to a display device which records directly, such as in a graph, the distribution of the particles in the sample.

14 Claims, 8 Drawing Figures

PARTICLE SIZING APPARATUS

BACKGROUND OF THE INVENTION

The invention relates, in a general way, to the field of analyzing particles and more particularly to measuring their distribution, so that the measurements can be employed directly, for example, in the form of graphs. The particles concerned in this invention may be biological cells contained, for example, in blood, powdered products used in industry, or emulsions and the like.

DESCRIPTION OF THE PRIOR ART

Such particles can be counted and their dimensions measured by known apparatuses, and more particularly by an apparatus which employs the principle of passing the particles in a suspension through an electrical detection zone of such dimensions that the presence of each particle markedly changes the impedance of the zone. This impedance change is employed so as to produce an electrical pulse whose duration is equal to the time necessary for the particle to pass through the detection zone and whose amplitude is proportional to the volume of the particle.

This principle is known as the "COULTER principle" and an apparatus employing it is described in U.S. Pat. No. 2,656,508 designated as Model A, an improvement thereof being described in U.S. Pat. No. 3,259,842, designated as Model B.

The COULTER principle is advantageously, although not in a limiting way, applied in the present invention since the electrical signals produced by the particles in accordance with this principle depend, for all practical purposes, on the volumes of the respective particles regardless of their configuration. Thus, the signal due to a given particle is proportional to the mass or true volume of this particle.

It will be understood that as there exist apparatuses which are capable of counting the number of the particles of a sample or specimen and measuring their dimensions, it is possible to carry out sequential measurements and calculate by means of successive sections or ranges the masses of each of these sections and deduce therefrom the total distribution of mass or volume.

Heretofore, no detector has been in existence which was capable of carrying out this operation rapidly, that is automatically and directly, merely by the passage of a sample therethrough. For example, the aforementioned COULTER-type detector or counter, in world-wide use at the present time, furnishes data concerning the dimensions and numbers of the particles in the sample, whereby it is possible, by means of these data, to establish various graphs representing, for example, the integral and the derivative of the dimension as a function of the number counted and the volume of particles. The drawing up of these graphs is a tedious procedure since it requires very long and exacting calculations and numerous operations.

Therefore, to ascertain a distribution of volume or mass by means of the COULTER-type detector or counter or any other existing type of apparatus, it is necessary to record numbers of accumulated particles ranging from the largest particles to the smallest and to also record the characteristics of the various adjustments of sensitivity of the detector which define the threshold, below which the spectrum of the distribution of the particles contained in the sample being analyzed is "cut off," and only the particles of a size greater than this threshold appear in the counting of a section of a given size. The various adjustments of sensitivity furnish values which correspond to a "volume index" pertaining to each size of considered particles, this index being designated hereinafter by the letter $p$. The volume or mass index or, in other words, the value of $p$, defines in the graph representing the distribution spectrum the "divisions" established in the course of the analysis or, in other words, the successive particle size sections of the considered sample.

The conventional method, namely the manual calculation for establishing a mass distribution, for example as a per cent figure of the total mass of particles of the sample, comprises first recalculating the analysis results giving the accumulated counts obtained for the various particle sizes, in differential values.

For example, in $N_1, N_2, N_3, N_4 \ldots$ represent each, the quantity of particles of a certain size, $\Delta N_1, \Delta N_2, \Delta N_3$, etc. are being calculated. Thereafter, the volume indices $p_1, p_2, p_3 \ldots$ which are of course different for each particle size section, are on average taken in pairs. The calculation is therefore as follows:

$$\frac{p_n + p_{n+1}}{2} = p_a \quad , \quad \frac{p_{n+1} + p_{n+2}}{2} = p_b, \text{ etc.,}$$

which furnishes the mean indices of volume of the differential sections of the sizes in question. The products $p_a \Delta N_1, p_b \Delta N_2, p_c \Delta N_3$, etc., then give an image of the masses of the successive sections in the sample being analyzed.

Generally, a distribution of this type is carried out in about 10 to 20 sections, starting with the section of the largest size, that is, with the highest volume index $p$. The number of sections determines the precision of the curve it is desired to obtain at the end of the measurement. The addition of all the sections is the image of the total mass of particles $\Sigma \Delta N$. It is then easy to obtain the mass percentage of each class by a manual calculation.

The object of the invention is to provide an electronic apparatus which automatically carries out each aforementioned calculating operation and directly displays the result of the measurements, that is, the mass distribution of a sample by means of a curve tracer, a printer associated with an analog-to-digital converter or another suitable display device.

SUMMARY OF THE INVENTION

The invention provides an electronic apparatus for furnishing a mass or volume distribution of a sample of particles having various sizes, comprising detecting means capable of generating sequentially, in the course of an analysis of a given sample, a series of electrical pulse trains at the rate of one pulse per particle, each pulse representing the volume or the mass of said particle, said detecting means comprising means establishing a sequentially variable threshold of sizes so that the appearance of said pulses is conditioned for each successive value of said threshold only by the particles whose sizes exceed said value, said apparatus comprising sequential counting means connected to said detecting means so as to receive and count the pulses contained in said pulse trains and furnishing in synchronism with the variation of said threshold and with successive receptions of said pulse trains, a series of output signals, measuring means for measuring the time which elapses between the start of each counting carried out by said counting means and the appearance of the corresponding output signal, so as to establish signals whose durations represent the numbers of counted particles for the respective threshold values, differential calculating means for sequentially counting values representing the difference between each pair of successive durations thus obtained, and display means for successively displaying said differential values.

Thus it can be seen that the apparatus according to the invention establishes by counting means a series of signals which determine periods whose lengths are variable in accordance with the considered particles section. These lengths therefore take into account both the size of the particles and the number of particles established for each size in each measuring section. Consequently, the factors $p_aN_1$, $p_bN_2$, etc., are converted into values of time, which has the advantage of permitting utilization of extremely simple circuits, mainly integrators, which are relatively simple to use. The cost of the apparatus can thus be relatively low, whereas the measurements are carried out entirely automatically with no need for manual calculating operations.

Further features and advantages of the invention will be apparent from the ensuing description with reference to the accompanying drawings.

DESCRIPTION OF THE PREFERRED EMBODIMENTS

Figure 1:
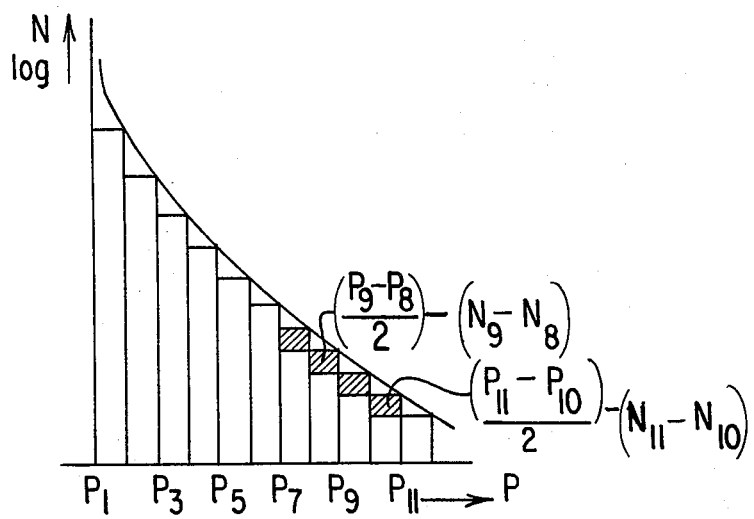
FIG. 1 is a graph illustrating the calculating method employed by the apparatus of the invention.

The analyzing apparatus according to the invention permits obtaining directly analog values of the mass or volume distribution or particles of a given sample or specimen. Such sample can be, for example, a quantity of blood, or a sample of industrial nature. Each sample analysis is carried out sequentially by dividing the measurements into several sections, ranges or sequences which represent respective sizes of the particles as shown in the graph of FIG. 1.

Figure 2:
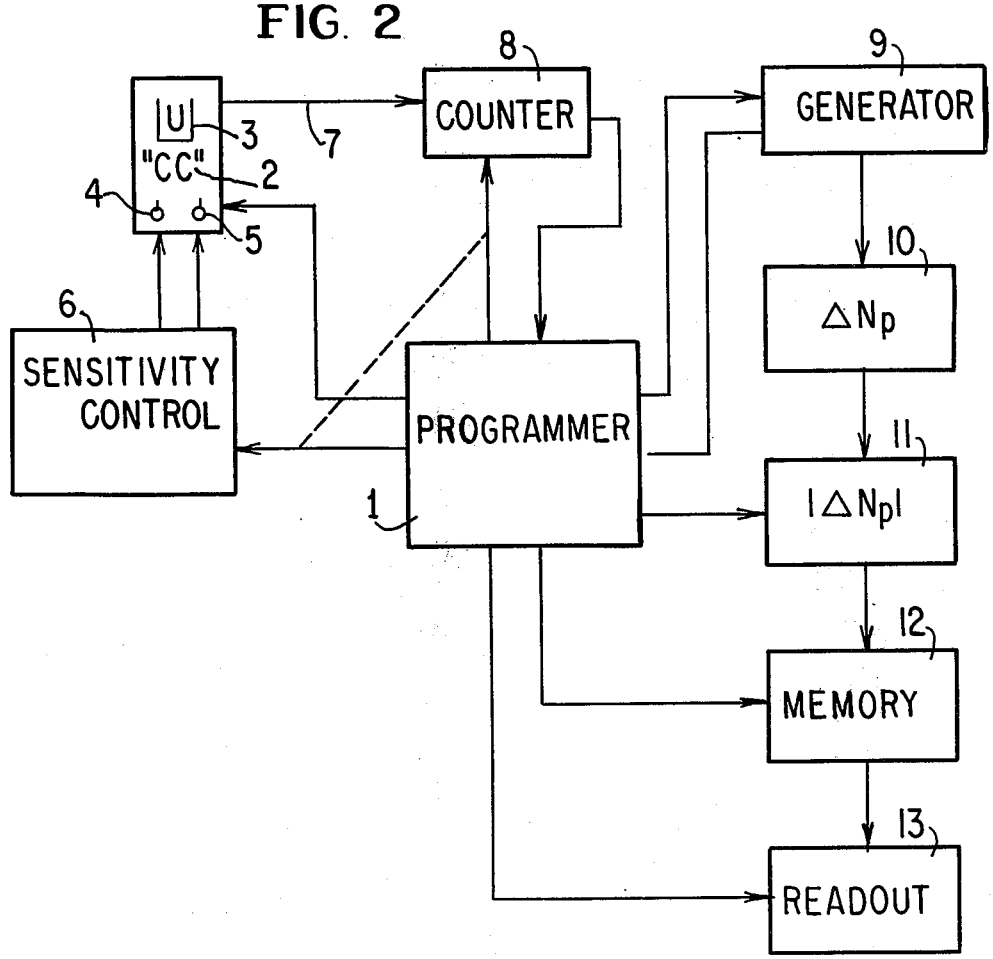
FIG. 2 is a block diagram of a particle analyzing apparatus according to the invention.

In order to obtain analyzing sequences, the apparatus is provided, as illustrated, in the embodiment of FIG. 2, with a programmer 1 which may be of any suitable type, for example, an electromechanical programmer. In the latter case, it comprises a stepping switch which carries out one step for each section of the measurement. The programmer controls the operation of all other circuits of the apparatus.

The sample is introduced into the particle counter 2 which is of the type in which each particle of the sample produces as a rule one electrical pulse (neglecting inaccuracies which might result from coinciding particles) whose amplitude and shape are representative of the volume or the mass of said particle.

A well-known counter of this type is the counter based on the "COULTER principle" which is described in detail in the aforementioned U.S. Pat. No. 3,259,842. Such counter is provided in a well-known manner with an analyzing tube 3 having an orifice through which a conduction path is established whose impedance is modified by the particles passing through the orifice. The resulting pulses are amplified and employed for counting the particles. The sensitivity of this counter can be regulated or adjusted by varying the electrical current passing through the conduction path. Further, the amplifying factor of the apparatus can be varied, the controls being schematically indicated by knobs 4 and 5. The invention utilizes the fact that these two control factors constitute a threshold value which enables determining the aforementioned distribution sections. Indeed, for given regulations of the orifice current and the gain of the counter, only those particles exceeding a certain threshold value will give rise to measurable pulses. In other words, the two current and gain regulations permit varying the sensitivity threshold of the counter. Therefore, if a high threshold is set, only particles of large sizes will be detectable, whereas if the threshold is adjusted to be low, all particles exceeding this threshold value will be detected.

In the apparatus according to the invention, the concomitant current and gain regulations determine the factor $p$, already mentioned, which preferably is varied, for reasons of convenience, by a factor which can be easily expressed by electronic circuits. Thus, a variation of 2 per section is preferably chosen, although other values, for example the value $\sqrt{2}$, can also be employed to advantage, as will be clear from the ensuing description.

Consequently, in FIG. 1, all the illustrated sections have the same width, $p_1$ being equal to ½ $p_2$ and to ¼ $p_3$, etc.

In the analyzing apparatus according to the invention, the manual regulating knobs 4 and 5 usually provided on a COULTER-type counter are not employed but a special sensitivity regulating circuit, represented by the reference numeral 6 in FIG. 2 is added to the counter. This regulating circuit is controlled step-by-step by the programmer 1, and therefore furnishes to the counter 1 the factors $p$ necessary for establishing in succession the thresholds of the analyzing sequence. It is then possible to count merely the number of particles giving rise to measurable pulses in each analyzing section to obtain the graph shown in FIG. 1. It will be understood that it is possible to arrange for each section a given counting time which would remain constant throughout the measurement and to count the particles of this section. However, the values obtained in this way could only be treated at the price of a considerable complication of the apparatus and this is why this method has not been considered here. Therefore, the invention does not teach how to utilize a number of particles in each section as a measurement magnitude but the time that each section takes to be filled up to a given number of particles, determined by the factor $p$. It is, therefore, the duration of each consecutive measurement of a section which constitutes the important parameter of the measurement. Indeed, the magnitude of time is easy to treat in analog analysis circuits and this greatly simplifies the apparatus of the invention.

The pulses produced by the detector 2 appear on a line 7 and are applied to a binary counter 8, a detailed description of which will be given hereinafter with reference to FIG. 3. The counter 8 is also controlled by the programmer 1 and itself causes the advance of the latter after the filling of each section up to the predetermined number of particles pertaining to the considered section. Therefore, at the end of each sequence corresponding to a section of the measurement, the programmer 1 delivers a signal which triggers a generator 9 which delivers sequentially at its output a magnitude $T_n = kN_n p_n$ in which $T_n$ is the interval of time, $k$ a constant, $N_n$ the number of particles per section and $p_n$ the aforementioned threshold factor.

The generator is followed by a differential calculator 10 which gives the magnitude $\Delta N_p$ or, in other words, the values $$\left(\frac{p_n - p_{n-1}}{2}\right)\left(N_n - N_{n-1}\right)$$

of successive sections.

The differential calculator delivers an output signal to a second calculator 11 which establishes the magnitude $|\Delta N_p|$ and delivers a positive voltage proportional to this value. Section by section, the magnitudes thus established are stored in a sequential memory 12 which memorizes all the values and calculates the sum at the end of the measurement. Meanwhile, this memory is capable of delivering distinct values to a reading device 13 which may be of any appropriate conventional type, for example a printer, curve tracer, oscilloscope, etc.

Figure 3:
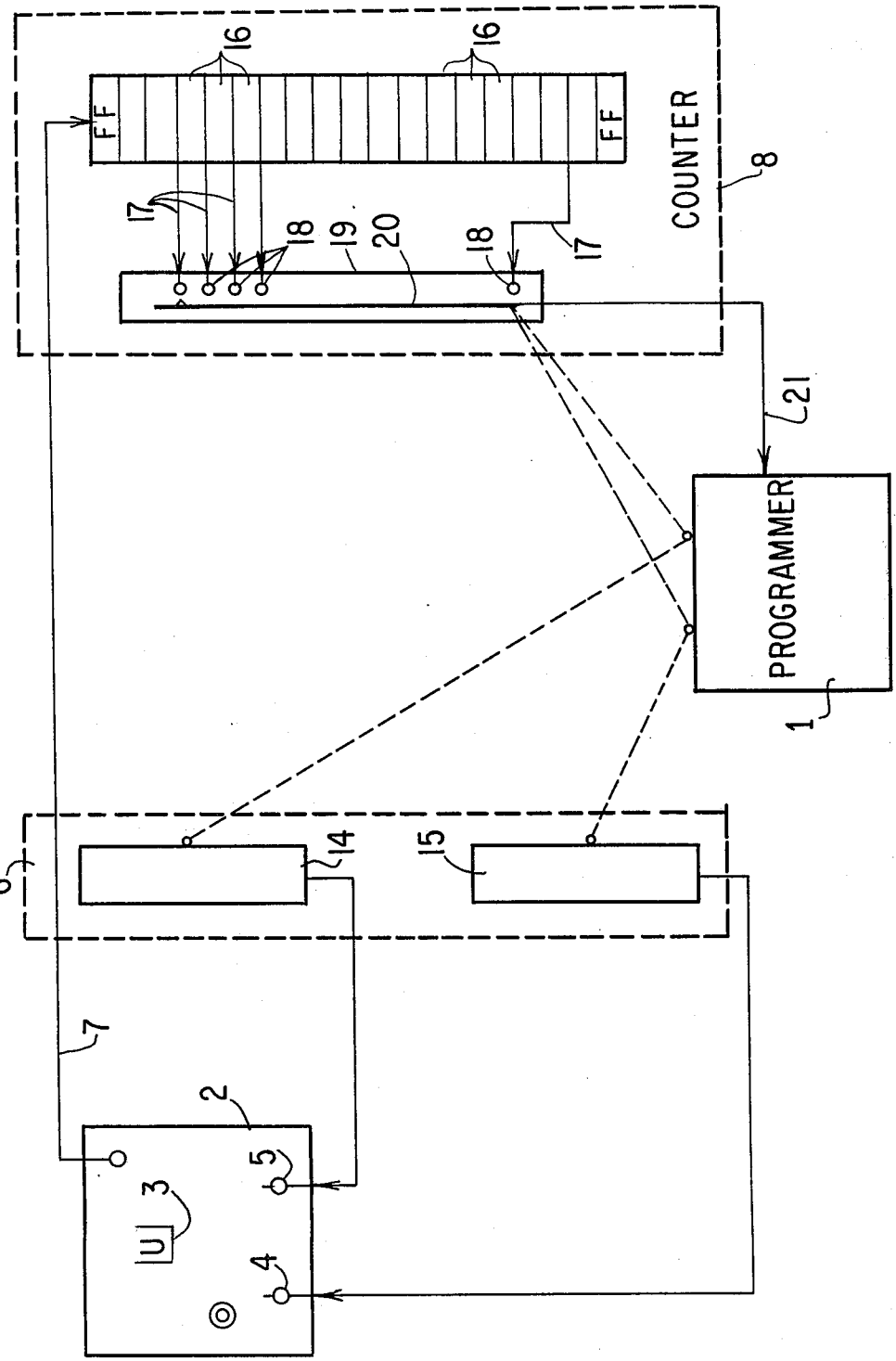
FIG. 3 is a schematic diagram of a calculating circuit for establishing the factor $N_np_n$.

FIG. 3 shows the principle of operation of the binary counter 8. There is shown the COULTER COUNTER 2 with its orifice tube 3 and the manual control devices 4, 5 for the gain and the orifice current. Since the devices 4 and 5 are not employed, they are connected to the sensitivity control circuit 6 which has two attenuators 14 and 15, which are controlled sequentially by the programmer 1 and thus establish the factors $p_1$, $p_2$, $p_3$, etc., which form in the illustrated embodiment a geometric progression having a ratio of 2.

The counter 8 comprises a number of counting units 16 which are arranged such as to reproduce a geometric progression having a ratio of 2. The counting units may be constituted in the known manner by, for example, flip-flops. Each counting unit has an output 17 which is connected to a corresponding stud 18 of a switch 19 whose moving contact 20 is controlled by the programmer 1. The latter in successively passing through each analyzing section, simultaneously regulates the attenuators 14 and 15 in a progression having a ratio 2 and switches the moving contact 20 successively onto the information terminals or outputs 17 of the network of counting units 16.

The pulses coming from the detector 2 through the line 7 are applied to the input of the counter. For reasons of statistical precision, the first three units of the counter are not employed directly. Therefore, if the switch 19 is placed on the first stud 17, a pulse will appear at this stud when eight pulses have been furnished by the line 7. On the following stud, a pulse appears if 16 pulses are counted, etc. If, for example, 16 analyzing sections are chosen, that is, 16 studs 18 and 19 counting units, the variation can therefore be by $2^{16}$, namely 32,768 and the factor $p$ can therefore vary in the same ratio. The respective output pulses of the counting units are fed back into the programmer 1 through a line 21.

As already mentioned, the number of particles per measuring section or sequence is obtained from the duration of the filling of the counter 8 for a considered section. Indeed, the filling interval of time is not only a function of the position of the switch 19, and therefore of the factor $p_n$, but also of the frequency of the counting pulses appearing on the line 7 for the considered measuring section. Consequently, the time parameter which is obtained for each measuring sequence is proportional to $1/N_n p_n$.

The synchronization of the attenuators 14 and 15 and of the switch 19 by the programmer therefore permits obtaining the factors $1/N_1 p_1$, $1/N_2 p_2$, $1/N_3 p_3$, etc. The relation $1/N_n p_n = T_n$ explains why the counter operates in fact in accordance with a geometric progression having a ratio of ½.

The output pulse of the signal of the binary counter 8 appearing on the line 21 permits determining each end of a measuring sequence, the programmer establishing, each time, the start. The interval $T = 1/N_n p_n$ is therefore counted between the moment when the programmer starts a sequence and the moment when an output signal appears at one of the outputs 17 of the counter.

Figure 4:
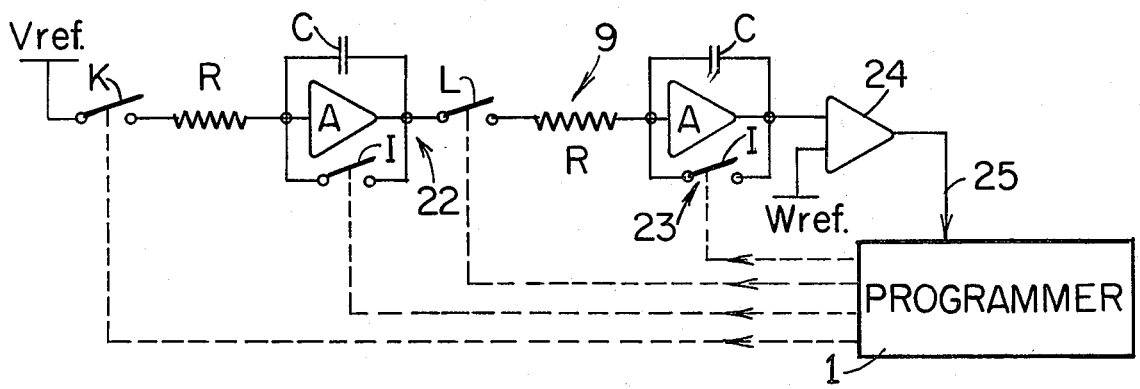
FIG. 4 is a general diagram of a signal generator establishing an output voltage in relation to $T = kN_np_n$.

As the programmer 1 receives these output signals, it also controls the operation of the generator 9, which will now be described with reference to FIG. 4.

The generator 9 comprises two integrators 22 and 23 each of which includes an amplifier A, an input resistor R and a parallel capacitor C. Each amplifier A can be shunted by a switch I controlled by the programmer 1. The resistor R of the integrator 22 is connected to a switch K controlled by the programmer 1. It closes at the start of each sequence and opens again at the end, that is, when an output signal appears at one of the output 17 of the counting units 16. The other terminal of the switch K is connected to a source of a reference voltage $V_{ref}$.

When the programmer controls the start of a measuring sequence, the switch K brings into action the integrator 22 which establishes an output voltage $V_{s-22}$:

$$V_{s-22} = \frac{1}{RC} \int_o^{T_n} V_{ref}. \, dT_n$$

As $V_{ref}$. is a scale of constant voltage, $V_{s-22}$ can be written:

$$V_{s-22} = \frac{1}{RC} V_r T_n$$

wherein $T_n$ is the interval of counting determined by one of the positions $n$ of the moving contact 20 of the switch 19 with respect to the series of counting units 16.

Thus:

$$V_{s-22} = K_n T_n = K \frac{1}{N_n P_n},$$

the switch $K$ being open at the end of the measuring sequence, that is, when a pulse appears on the line 21.

The output of the integrator 22 is connected to the input of the integrator 23 through a switch L which is also controlled by the programmer 1. The output of the integrator 23 is connected to a comparator 24 whose second input is connected to a reference source $Wref$.

Consequently, when the counting of the pulses of the considered sequence has finished, the first integrator 22 stops and the second integrator 23 is brought into action by the closure of the switch L. The integrator 23 then operates until its output voltage equals the reference voltage $Wref$, whence:

$$V_{s-23} = \frac{1}{RC} \int_0^{T_x} V_{s-22} \, dT_x$$

As $V_{s-22}$ is here a constant, since the switch K is held open, there can be written:

$$V_{s-23} = \frac{1}{RC} V_{s-22} T_x \text{ or } T_x = RC \frac{V_{s-23}}{V_{s-22}}$$

As at the end of the integration $V_{s-23}$ equals $Wref$, which is known, there can be written:

$$T_x = \frac{Wref}{V_{s-22}} = \frac{K_x}{V_{s-22}}$$

As, moreover, $$V_{s-22} = \frac{K_n}{N_n P_n}$$

there is obtained:

$$T_x = k_y N_n p_n$$

with $K_Y = k_n \cdot K_x$

This explanation is obviously identical for each measuring sequence so that it may be concluded that the operating time $T_x$ of the integrator 23 is proportional to $N_n p_n$, that is, to the volume of the particles measured in the section of the considered particle size.

It will be understood that before the beginning of each measuring sequence, the programmer 1 empties the integrators 22 and 23 by means of the switches I. The voltage proportional to $T_n$ appears at the output terminal 25 of the interval generator 9.

Figure 5:
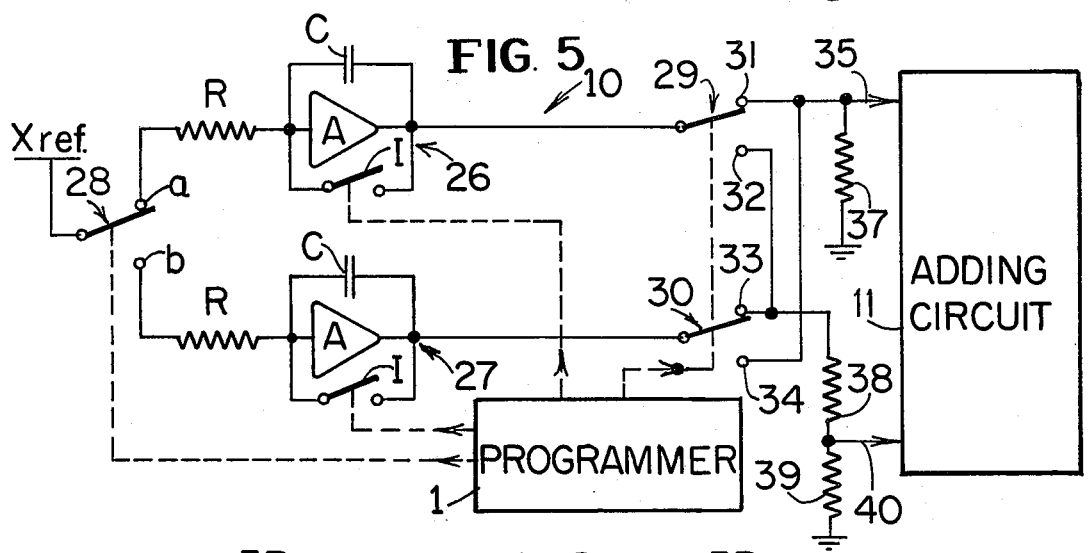
FIG. 5 is a differential calculating circuit for establishing the magnitude $\Delta N\bar{p}$.

FIG. 5 shows the circuit of the differential calculator 10 establishing the magnitude $\Delta \bar{N}_n \bar{p}$. This circuit comprises two integrators 26 and 27 each of which is provided with an input resistor R, an amplifier A, a parallel capacitor C and a short-circuit switch I, all of which are controlled by the programmer 1. The resistors R of the two integrators can be connected alternately to a source of reference $Xref$ by means of a switch 28 controlled by the programmer 1. The outputs of the integrators 26 and 27 are respectively connected to the moving contacts of two switches 29 and 30. The first fixed contact 31 of the switch 29 is connected to the second switch contact 34 of the switch 30 and to one of the inputs 35 of an adding circuit which is the circuit 11 (FIG. 2) establishing the magnitude $|\Delta N_{\bar{p}}|$ in the form of a positive voltage.

A resistor 37 of value S grounds this input. The second fixed contact 32 of the switch 29 is connected to the first fixed contact 33 of the switch 30 and to a voltage divider having two resistances 38 and 39 of value ½ S respectively, their junction being connected to a second input 40 of the adding circuit 11. The voltage divider is moreover connected to ground.

The operation of the switches 28, 29 and 30 and the switches I is again controlled by the programmer 1.

At the start of a given sequence $n$, the integrators 26 and 27 are at zero, their switches I being preliminarily closed for a certain time. The switch 28 is placed at contact 28a as soon as the switch L (FIG. 4) of the integrator 23 of the generator 9 is closed.

Consequently:

$$V_{s-26} = \frac{1}{RC} \int_0^{T_x} Xref \, dT$$

As the voltage $Xref$ is a constant, there is obtained:

$$V_{s-26} = K_z T_x = K N_n p_n$$

The integrator 26 therefore operates simultaneously with the integrator 23.

At the end of the sequence $n$, voltage $V_{s-26} = K N_n p_n$ is stored by the integrator 26 and the following sequence $(n+1)$ starts. When the switch L of the generator 9 is once again closed, the switch 28 applies the voltage $Xref$ to the integrator 27 which produces a voltage $V_{s-27} = N_{n+1} p_{n+1}$.

As already mentioned, the factor $p$ follows a geometric progression having a ratio of 2 so that for two consecutive sequences:

$$p_{n+1} = \frac{p_n}{2}$$

Indeed, in the chosen example, the analysis is started with the largest particles corresponding to the highest factor $p$ and the geometric progression is followed with the inverse ratio, which is required by the binary counter.

As, moreover:

$$\Delta N = N_{n+1} - N_n$$

it is sufficient to subtract the value of the output voltage of the integrator 27 from the output voltage of the integrator 26 and to divide the latter by a factor 2 to obtain the value $\Delta N \bar{p}$. This manner of calculating is of course valid for alternating measuring sequences, provided that the switches 28, 29 and 30 are suitably actuated. The following differential relation is thus obtained:

$$N_{n+1} \cdot p_{n+1} - \frac{N_n p_n}{2} = \Delta N_{\bar{p}}$$

It can be seen that the circuit shown in FIG. 5 performs this operation by means of the three resistors 37, 38 and 39 and the adding circuit 11.

Indeed, in the illustrated position, the switch 29 applies the voltage $V_{s-26}$ which represents the actual value of the last measured section, that is, $N_{n+1} \cdot p_{n+1}$, at the terminal 35 of the adding circuit 11 with no other calculating operation by means of the resistor 37 of value S. On the other hand, the voltage $V_{s-27}$ representing the value of the previously measured section, namely $N_n \cdot p_n$, is applied to the voltage divider 38, 39 which divides it in two, the values of the resistors each being S/2. The divided voltage is applied to the terminal 40 of the adding circuit 11 which establishes the aforementioned difference.

For the following sequence, the voltage $V_{s-26}$ represents the value $N_{n+2} \cdot p_{n+2}$ and the voltage $V_{s-27}$ the value $N_{n+1} \cdot p_{n+1}$. As the switches 29 and 30 were actuated simultaneously, the differential operation is once again correctly carried out.

Figure 6:
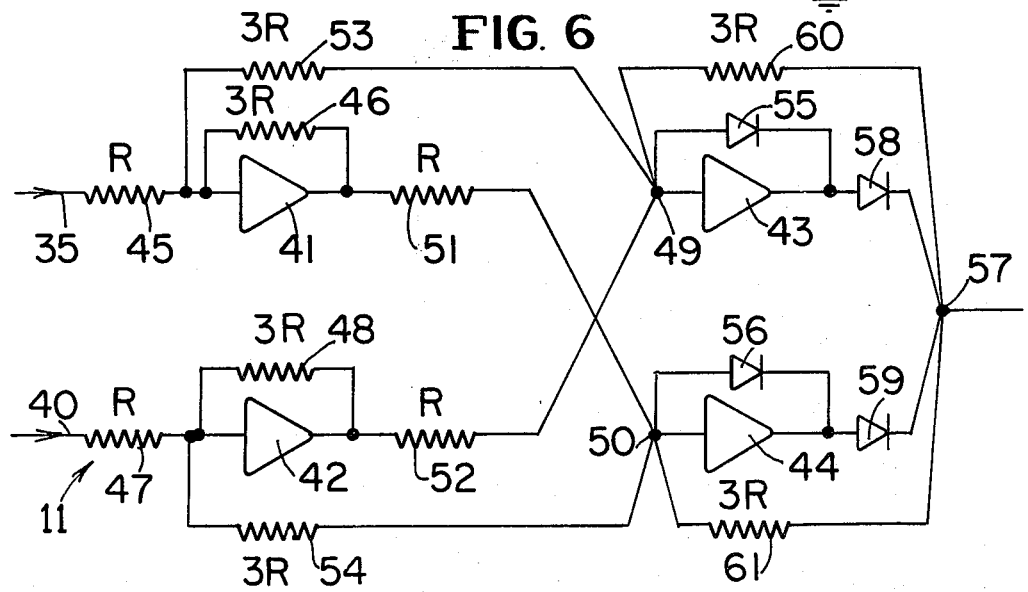
FIG. 6 is a calculating circuit for establishing the value $|\Delta N\bar{p}|$ and producing a positive voltage proportional thereto.

The detail of the adding circuit 11 is shown in FIG. 6. This circuit comprises four amplifiers 41 to 44 connected in the following way:

The amplifier 41 is connected to the terminal 35 through an input resistor 45 of value R and shunted by a resistor 46 of value 3R. Similarly, the amplifier 42 is connected to the terminal 40 through a resistor 47 of value R and shunted by a resistor 48 of value 3R. The outputs of the amplifiers 42 and 41 are respectively connected to two junction points 49 and 50 through resistors 52 and 51 of value R.

A resistor 53 of value 3R connects the input of the amplifier 41 to the junction point 49 and a resistor 54 of value 3R connects the input of the amplifier 42 to the junction point 50.

The amplifiers 43 and 44 are respectively shunted by diodes 55 and 56, their outputs being connected to a junction point 57 through diodes 58 and 59 respectively. The point 57 constitutes the output of the circuit. The junction points 49 and 50 are connected to the junction point 57 through resistors 60 and 61, respectively, of value 3R.

The voltages applied to 35 and 40 being for example $U_1$ and $U_2$ (namely $N_{n+1} \cdot p_{n+1}$ and $N_n p_n/2$) the following relations can be written:

$$U_{s-41} = -\tfrac{1}{3} U_1 \text{ and}$$

$$U_{s-42} = -\tfrac{1}{3} U_2 \; (s = \text{output})$$

$$U_{e-43} = U_{e-44} = 0 \; (e = \text{input})$$

Therefore, the voltage $U_{s-57}$ appearing at the terminal 57 is equal to $$U_1 + 3 U_{s-42} = U_1 - U_2$$

or $$U_2 + 3 U_{s-41} = U_2 - U_1$$

As the diodes 55, 56 and 58, 59 prohibit a negative sign for the voltage $U_{s-57}$, the following relations are obtained:

$$U_{s-57} = U_2 - U_1 \text{ if } U_2 > U_1$$

$$U_{s-57} = U_1 - U_2 \text{ if } U_2 > U_2$$

Therefore, the desired value $\Delta N\bar{p}$ appears at the output terminal 57 of the adding circuit 11 in the form of a positive voltage.

Figure 7:
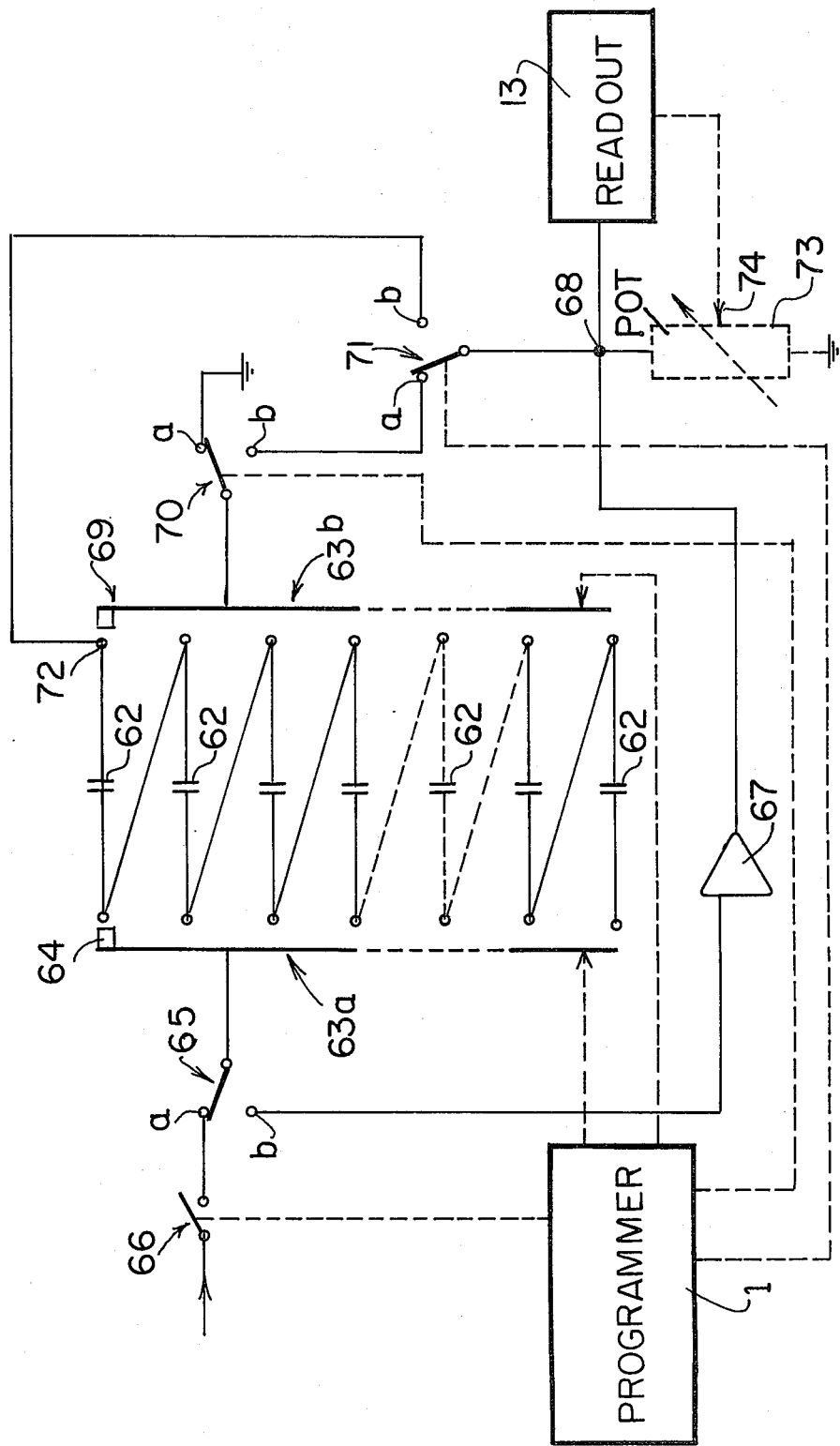
FIG. 7 is a diagram for reading individual values of $\Delta N\bar{p}$ for each particle size section and establishing the value of $\Sigma|\Delta N\bar{p}|$.

The sequential memory which successively stores all the values $\Delta N\bar{p}$ thus calculated is shown in FIG. 7. This memory comprises a series of very high quality capacitors 62, for example of the "Mylar" type, which are connected in series. Each of their respective terminals is moreover connected to a stud of a bi-pole switch 63a, 63b which is controlled by the programmer in synchronism with the switch 19 of the counter 8 (FIGS. 2 and 3). There are as many capacitors as there are successive measuring sections. The slider 64 of one of the halves 63a of the bi-pole switch is connected to the moving contact of a switch 65 controlled by the programmer 1. The fixed contact a of this switch 65 is connected to the junction point 57 of the adding circuit 11 (FIG. 6) through a switch 66 also controlled by the programmer 1 as to close once at the end of each measuring sequence.

The fixed contact b of the switch 65 is connected to a very high gain amplifier 67 whose output is connected to a junction point 68. The slider 69 of the second half of 63b of the bi-pole switch is connected to the moving contact of a switch 70 having a fixed contact a connected to ground. The other fixed contact b of switch 70 is connected to one of the fixed contacts a of a switch 71 whose moving contact is connected to the junction point 68. The other fixed contact b of the switch 71 is connected to the terminal 72 of the first capacitor 62 which is not connected to the following capacitor 62. The junction point 68 can be connected either directly to the display device 13 or through a potentiometer 73 connected between the point 68 and ground and whose slider 74 is connected to the display device.

At the end of each measuring sequence, with the exception of the first, of course, the adding circuit transmits the corresponding value $\Delta N\bar{p}$ to the corresponding memory capacitor 62, the switches 65 and 70 being placed in the position shown in FIG. 7 and the switch 66 being closed. When the storing is completed, the programmer 1 opens the switch 66 and the switch 63a, 63b makes a step simultaneously with the switch 19 and the measurement is again carried out for the following section. The storing of the following value $\Delta N\bar{p}$ occurs when the switch 66 is closed by the programmer 1. Therefore, the operation is carried out sequentially until the last value $\Delta N\bar{p}$ has been stored in the capacitor 62 at the bottom of FIG. 7. After the latter operation, the switch 66 opens and the switches 65 and 70 switch to the contact 65b and 70b and allow the apparatus to restore the stored results. When the switch 75 is on contact 71b, the capacitors 62 are connected in series and the assembly is applied to the terminals of the amplifier 67 which allows the operator to calibrate the cumulative 100% by means of the potentiometer 73. the rotation of the switch 63a–63b therefore permits restoring the cumulative progressive values ($\Delta N\bar{p_a} - \Delta N\bar{p_a} + \Delta N\bar{p_b} - \Delta N\bar{p_a} + \Delta N\bar{p} + \Delta N\bar{p_c} \ldots \Delta n\bar{p_x}$).

When the switch 75 is on the contact 75a, the capacitors 62 are taken back separately and successively applied to the amplifier 67 which permits the restoration of the percentages as differentials, that is, per section ($\Delta N\bar{p_a} - \Delta N\bar{p_b} - \Delta N\bar{p_c} \ldots \Delta N\bar{p_x}$).

The display device 13 can be an X–Y tracer whose X axis operates in synchronism with the programmer. However, the information taken from the terminal 68 can be kept for another display system (oscilloscope or other means) or be transformed into a digital information for feeding into a digital counter through an analog-to-digital converter of suitable type (not shown).

Following are particulars of the automatic system for analysis control and procedure (not shown).

I — VALUES FOR $nt$ —

The volume of the particles collected in a classification is defined by the number of particles. Consequently, the dilution rate and the size distribution of the sample work upon the values obtained in a rank. The machine can measure this information with a relation of 1000 between the lowest value and the highest.

Definition of the dynamics for a considered classification

It is the relation of the possible counting times for a considered classification.

For instance:

First classification: 8 pulses counting of a defined volume.

This counting can be achieved within

| 20 seconds | maximum | Relation |
|---|---|---|
| 20 m. " | minimum | 1000 |

First case: $nt = 0$, i.e., less than 8 pulses in 20 seconds for the first classification. A comparator delivers a command voltage driving to the reading $nt + 0$ and the switching of the first stage of the counting chain.

The second analysis classification will thus be done with a determination upon 8 pulses and not 16 as it is normally foreseen.

The maximum possible counting time still being 20 seconds, the classification measuring possibility is thus doubled.

If the $nt$ value is still null, the comparator commands a new signal and suppresses a second classification of the binary chain allowing a determination upon 8 instead of 32 of the third classification.

This possibility only exists for three classifications of the binary chain, i.e., division into 8, for statistical precision, because the third information indicates that the suspended sample must be detected with a smaller orifice, or that the dilution rate is too low. The spectrum confirms this indication.

However, this indication does not lock in the analyzer and, if he wants it so, the operator can go on with the analysis without modifying his detection system but not under as good conditions.

Second case: $nt$ too high, i.e., more than 8 pulses within 20 m.seconds for the first classification. A comparator delivers a command voltage driving to the readout of an alarm indicating to the operator it is necessary to dilute the sample again, or that the orifice is too small. It is a range of modification of the detection conditions. The analysis cannot be carried out without deteriorating results.

II — DETERMINATION OF THE END OF THE ANALYSIS —

At the end of each sequence, a system measures the relation $$\frac{\Delta n}{\Sigma \Delta n}$$

allowing to stop the analysis whenever this relation is inferior to the one chosen by the operator. (For instance <2%).

The operator can avoid this possibility for the control of a double population or simply checking that the whole of the assessment is effectively detected.

III — CALIBRATION —

The analyzer calibration counted with a counter can be achieved before each analysis or before each type of analysis. (Calibration depending upon the orifice impedance with the utilized diluent.)

To do so, it suffices to present particles with a known volume, i.e., reference particles, and to make the counter threshold coincide with the population crest after having looked for the best switch position, i.e., gain and aperture current.

With this threshold setting, the analysis determines — for each size classification — multiples and submultiples of 2 of the standard volume.

IV — 100% DETERMINATION —

The information $\Sigma \Delta nt$, sum of all the informations, is given to the operator at the end of the analysis. The operator must use this information as he would for a manual analysis.

If, for instance, he wants to make $\Sigma nt$ correspond to 98 or 99% a potentiometer gives him the possibility to lower this voltage allowing the readout at the chosen percentage. Each classification reading will be given directly.

Figure 8:
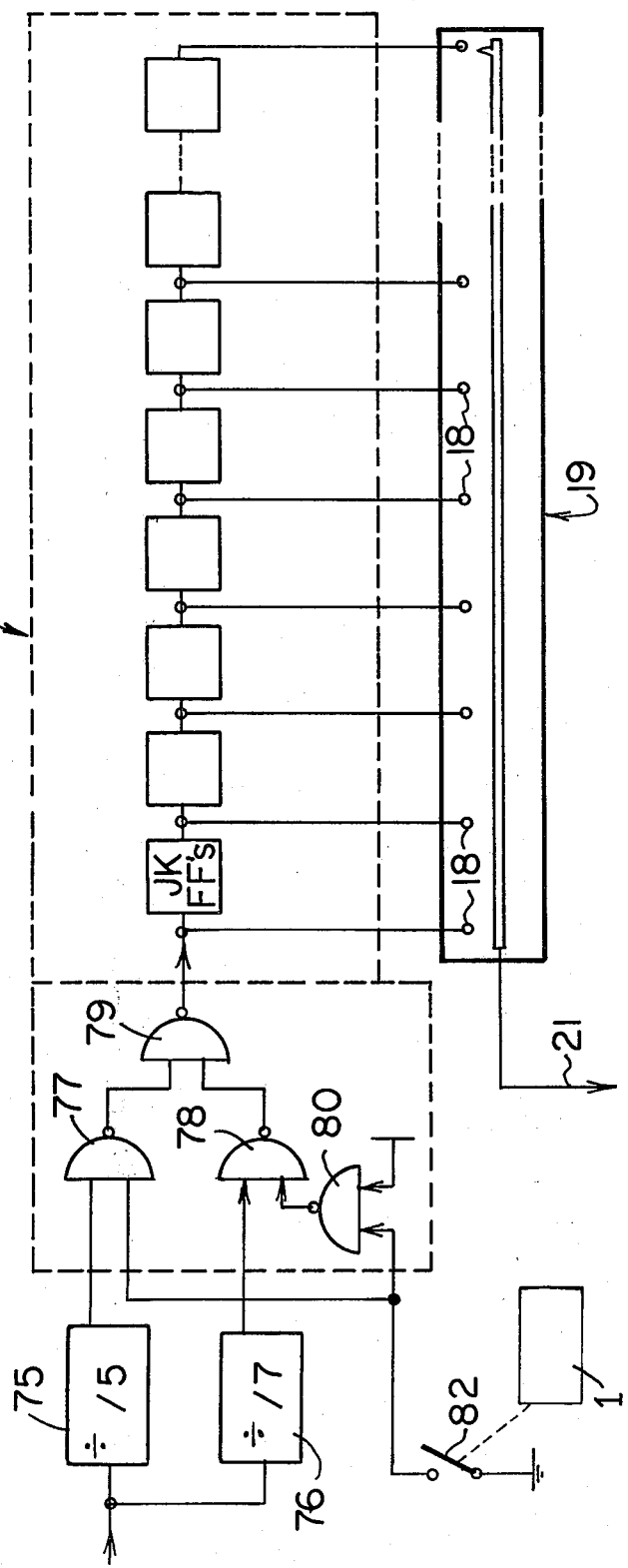
FIG. 8 is another embodiment of the calculating circuit for ascertaining the factor $N_np_n$.

FIG. 8 shows a modification of the invention in which there is employed a counter 8a which replaces the counter 8 shown in FIGS. 2 and 3. The counter shown in FIG. 8 establishes a geometric progression having a ratio $\sqrt{2}$ instead of the ratio 2. For this purpose, the circuit comprises two dividers 75 and 76 which divide respectively by 5 and by 7. The two dividers are connected to a logic circuit having four NAND gates 77 to 80 and whose output is connected to a series of J–K flip-flops constituting frequency dividers 81. The connecting points of the J–K flip-flops are individually connected to the studs 18 of the switch 19 which is identical to that shown in FIG. 3, the output of the counter being at terminal 21.

The pulses coming from the detector 2 (FIG. 1) are simultaneously applied to the dividers 75 and 76 which are constituted by decades, only the studs 5 and 7 of which are respectively employed. Consequently, with reference to the divider 75, there appears at the output of the divider 75 a negative logic level signal every five pulses. In respect of the divider 76, this signal appears of course every seven pulses.

To establish the inverse of the geometric progression having the ratio $1/\sqrt{2}$, there is employed a calculating artifice which consists in alternately dividing by 5 and 7 which gives in fact the following progression:

$$\frac{1}{5}; \frac{1}{7}; \frac{1}{10}; \frac{1}{14}; \frac{1}{20}; \frac{1}{28}; \frac{1}{40}; \frac{1}{56}; \text{etc.}$$

Note that in proceeding in this manner, it is accepted to introduce a slight error in the measurement which progressively increases from about 0.99% to 1.2% for the seventeenth term. Apart from the fact that this error only concerns the terms obtained by dividing by 7, the overall precision of the apparatus is easily maintained so that this error can be tolerated in practice.

The logic circuit comprising the gates 77–80 applies alternately the results of the division by 5 and by 7 to the counter in the following manner. One of the inputs of the gate 77 is connected to a switch 82 which is capable of applying thereto selectively the level of ground (0). This switch is also connected to one of the inputs of the gate 80 whose other input is permanently connected to the negative logic level (1). The circuit is so arranged that if the switch 82 is closed, the pulse coming from the divider 76 is transmitted to the series of flip-flops 81, whereas if the switch 82 is opened, it is the divider 75 dividing by 5 which transmits its pulse. Consequently, the switch 82 is actuated every other sequence in the course of the measurement, which is easily achieved by suitable circuitry in the programmer 1. The various factors $p$ are again transmitted in the form of durations to the programmer 1 which causes the generator to operate in the same manner as that described hereinbefore.

Variations are capable of being made without departing from the spirit of the invention as defined in the appended claims.

It is believed that the foregoing adequately will enable those skilled in the art to appreciate and practice this invention and, if necessary, make modifications which will fall within the scope thereof.

What it is desired to secure by Letters Patent of the United States is:

1. Apparatus for obtaining mass or volume distribution of a sample of particles having various sizes suspended in a fluid, said apparatus comprising:
    A. detecting means for sequentially producing a series of electrical pulse trains of one pulse per particle, each pulse representing the volume or mass of said particle, said detecting means including means for establishing a particle size threshold which is sequentially variable such that appearance of said pulses for each successive value of said threshold is contingent upon said particles having sizes exceeding said threshold value,
    B. sequential counting means connected to said detecting means for receiving and counting the pulses in said pulse trains and furnishing in synchronism with variations of said threshold a series of output signals, comprising a series of cascaded binary counting units including a multi-pole switch having a plurality of studs, the output of each of said binary counting units being connected to a stud of the multi-pole switch, and means for actuating said multi-pole switch in synchronism with the variation of said threshold,
    C. measuring means for measuring the time between the start of each counting and appearance of the corresponding output signals, such as to obtain signals having durations representing numbers of counted particles for the respective threshold values,
    D. differential calculating means for sequentially counting values representing the difference between each pair of successive durations thus obtained, and
    E. display means for successively displaying said differential values.

2. Apparatus as claimed in claim 1, wherein the cascaded counting units are constructed and adapted to define a geometric progression.

3. Apparatus as claimed in claim 2, wherein the ratio of the geometric progression is 2.

4. Apparatus as claimed in claim 2, wherein the ratio of the geometric progression is $\sqrt{2}$.

5. Apparatus as claimed in claim 4 comprising two dividing means connected in parallel and respectively dividing by 5 and by 7 said series of counting units being connected to the detecting means through said dividing means, logic circuit means for enabling connection of said dividing means alternately to said counting units in synchronism with the variations of said threshold.

6. Apparatus as claimed in claim 1, wherein the means establishing a threshold comprise two attenuators including means for respectively regulating the amplitudes of said pulses and the sensitivity of said detecting means.

7. Apparatus for obtaining mass or volume distribution of a sample of particles having various sizes suspended in a fluid, said apparatus comprising:
    A. detecting means for sequentially producing a series of electrical pulse trains of one pulse per particle, each pulse representing the volume or mass of said particle, said detecting means including means for establishing a particle size threshold which is sequentially variable such that appearance of said pulses for each successive value of said threshold is contingent upon said particles having sizes exceeding said threshold value,
    B. sequential counting means connected to said detecting means for receiving and counting the pulses in said pulse trains and furnishing in synchronism with variations of said threshold a series of output signals,
    C. measuring means for measuring the time between the start of each counting and appearance of the corresponding output signals, such as to obtain signals having durations representing numbers of counted particles for the respective threshold values, comprising:
        a. a first and a second integrator, the first integrator including means for integrating a constant voltage and being put into action thereby at the start of each counting and being stopped thereby as soon as said corresponding output signal appears, the second integrator including means for integrating the output voltage of the first integrator after said signal appears, and
        b. a comparator including means for causing stoppage of the second integrator upon detecting equality between a reference voltage applied thereto and the output voltage of the second integrator, wherein the interval of time which elapses between the start of the integrating operation of the second integrator and the instant when said comparator causes the stoppage of the operation of the second integrator represents said corresponding duration,
    D. differential calculating means for sequentially counting values representing the difference between each pair of successive durations thus obtained, and
    E. display means for successively displaying said differential values.

8. Apparatus as claimed in claim 7, comprising
    A. a third and a fourth integrator and
    B. means associated with said measuring means for utilizing the durations obtained in said measuring means to control alternately the operation of the third and fourth integrators, each of which include means for integrating alternately and during said respective durations a reference voltage, and other countings of said pulse trains, C. two voltage dividers coupled to the outputs of said third and fourth integrators including means for applying the integrated output voltages of said third and fourth integrators alternately and in synchronism with the operation of the integrators to the two voltage dividers for dividing said output voltages by factors which are in a ratio equal to the ratio of said geometric progression, and D. an adding circuit and means for applying the output voltages of the voltage dividers to the adding circuit.

9. Apparatus as claimed in claim 8, comprising
A. storing means, and means for applying the successive outputs of said adding circuit to the storing means individually and sequentially for each counting, and
B. means for adding the contents of the whole of the storing means at the end of the analysis.

10. Apparatus as claimed in claim 7, comprising a central programmer including means for synchronizing the entire operation of the apparatus, said last means including electromechanical control means.

11. Apparatus as claimed in claim 10 comprising
A. a first and second switch for putting into action said integrators of said measuring means, and
B. means associated with said programmer for controlling said switches.

12. Apparatus as claimed in claim 8 comprising:
A. a third switch connected on one hand to said reference voltage and on the other hand to the inputs of said third and fourth integrators,
B. a first and second bi-pole switch, the outputs of the last noted integrators being connected to the moving contacts of the bi-pole switches, the fixed contacts thereof being connected to said voltage dividers, and
C. a programmer including means for controlling said bi-pole switches.

13. An apparatus as claimed in claim 9 comprising:
A. two multi-pole switches,
B. said storing means including capacitors whose terminals are connected to the two multi-pole switches,
C. an amplifier adapted to furnish the sum of the voltages stored by said capacitors,
D. means to connect the moving contacts of the multi-pole switches selectively to the terminals of the amplifier, and
E. a programmer including means for controlling said multi-pole switches.

14. Apparatus as claimed in claim 13, comprising switching means, said capacitors being connected to the switching means, and including means for connecting the capacitors first successively and then together to said display means under the control of said programmer.

* * * * *

UNITED STATES PATENT AND TRADEMARK OFFICE
CERTIFICATE OF CORRECTION

PATENT NO. : 3,982,183
DATED : September 21, 1976
INVENTOR(S) : COLLINEAU, et al.

It is certified that error appears in the above-identified patent and that said Letters Patent are hereby corrected as shown below:

In column 1, line 28, read --Model "A"-- for "Model A";
In column 1, line 30, read --Model "B"-- for "Model B";
In column 2, line 6, read --"p"-- for "p";
In column 2, line 7, read --"p"-- for "p";
In column 3, line 54, read --of-- for "or";
In column 6, line 40, read --outputs-- for "output";
In column 7, line 52, read --$N_n\bar{p}$-- for "$\bar{N}_n\bar{p}$";
In column 7, line 65, read --$|\Delta N\bar{p}|$-- for "$|\Delta N\bar{p}|$";
In column 9, line 57, read --$U_s$-57 = $U_1$ - $U_2$ if $U_1 > U_2$-- for "$U_s$-57 = $U_1$ - $U_2$ if $U_2 > U_2$";
In column 10, line 14, before "63b" omit "of";
In column 10, line 16, after "b" insert --of--;
In column 10, line 47, read --The-- for "the";
In column 11, line 25, read --nt = O-- for "nt + O";
In column 13, line 4, read --("O")-- for "(O)";
In column 13, line 6, read --("1")-- for "(1)".

Signed and Sealed this

Eighteenth Day of April 1978

[SEAL]

Attest:

RUTH C. MASON
Attesting Officer

LUTRELLE F. PARKER
Acting Commissioner of Patents and Trademarks